US012564322B2

(12) United States Patent
Warburton et al.

(10) Patent No.: US 12,564,322 B2
(45) Date of Patent: Mar. 3, 2026

(54) HEAD-MOUNTED SYSTEM FOR MEASURING PTOSIS

(71) Applicant: Icahn School of Medicine at Mount Sinai, New York, NY (US)

(72) Inventors: Andrew Jinrui Warburton, New York, NY (US); Randal Alexander Serafini, New York, NY (US); Margarita Labkovich, New York, NY (US); Aly Al-Amyn Valliani, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 968 days.

(21) Appl. No.: 17/691,603

(22) Filed: Mar. 10, 2022

(65) Prior Publication Data

US 2023/0284899 A1 Sep. 14, 2023

(51) Int. Cl.
| | |
|---|---|
| *A61B 3/113* | (2006.01) |
| *G02B 27/01* | (2006.01) |
| *G06F 3/01* | (2006.01) |

(52) U.S. Cl.
CPC .......... *A61B 3/113* (2013.01); *G02B 27/0101* (2013.01); *G02B 27/017* (2013.01); *G06F 3/013* (2013.01); *G02B 2027/0138* (2013.01)

(58) Field of Classification Search
CPC ........ G02B 2027/0178; G02B 27/0176; G02B 2027/0138; G02B 27/0172;
(Continued)

(56) References Cited

U.S. PATENT DOCUMENTS

| | | | |
|---|---|---|---|
| 8,500,278 B2 * | 8/2013 | Lo | A61B 3/113 |
| | | | 351/209 |
| 2014/0031700 A1 * | 1/2014 | Ferrantelli | A61B 5/0077 |
| | | | 600/407 |

(Continued)

FOREIGN PATENT DOCUMENTS

WO      WO200810680      1/2008

OTHER PUBLICATIONS

Junoy Montolio, et al., "Factors That Influence Standard Automated Perimetry Test Results in Glaucoma: Test Reliability, Technician Experience, Time of Day, and Season", OVS, Oct. 2012, vol. 53, No. 11, 8 Pages.

*Primary Examiner* — Brandi N Thomas
(74) *Attorney, Agent, or Firm* — IP Spring

(57) ABSTRACT

A method to predict visual field loss includes defining a superior visual field as rows and columns in a coordinate system. The method further includes performing a display and record process for a first column of the columns by: initiating a base condition, initiating a recurrence condition, and initiating a stop condition when a difference between the new pivot point and a previous pivot point is less than a predetermined threshold. The method further includes repeating the display and record process for additional columns of the columns. The method further includes defining an eyelid meridian based on recorded coordinates for a set of points that are visible to the patient, calculating an area of the superior visual field based on the eyelid meridian, and determining the visual field loss based the area of the superior visual field.

20 Claims, 10 Drawing Sheets

(58) Field of Classification Search
CPC ...... G02B 2027/0187; G02B 2027/013; G02B
2027/0132; G02B 2027/0156; G02B
2027/0161; G02B 27/0103; G02B
27/0149; G02B 27/40; G02B 3/0006;
G02B 2027/0118; G02B 27/0101; G02B
27/017; H02J 50/402; H02J 7/35; H02J
7/0048; H02J 7/0049
See application file for complete search history.

(56) References Cited

U.S. PATENT DOCUMENTS

2016/0031702 A1     2/2016   Daneman et al.
2018/0131847 A1*    5/2018   Kokonaski .............. H02J 50/10

* cited by examiner

700

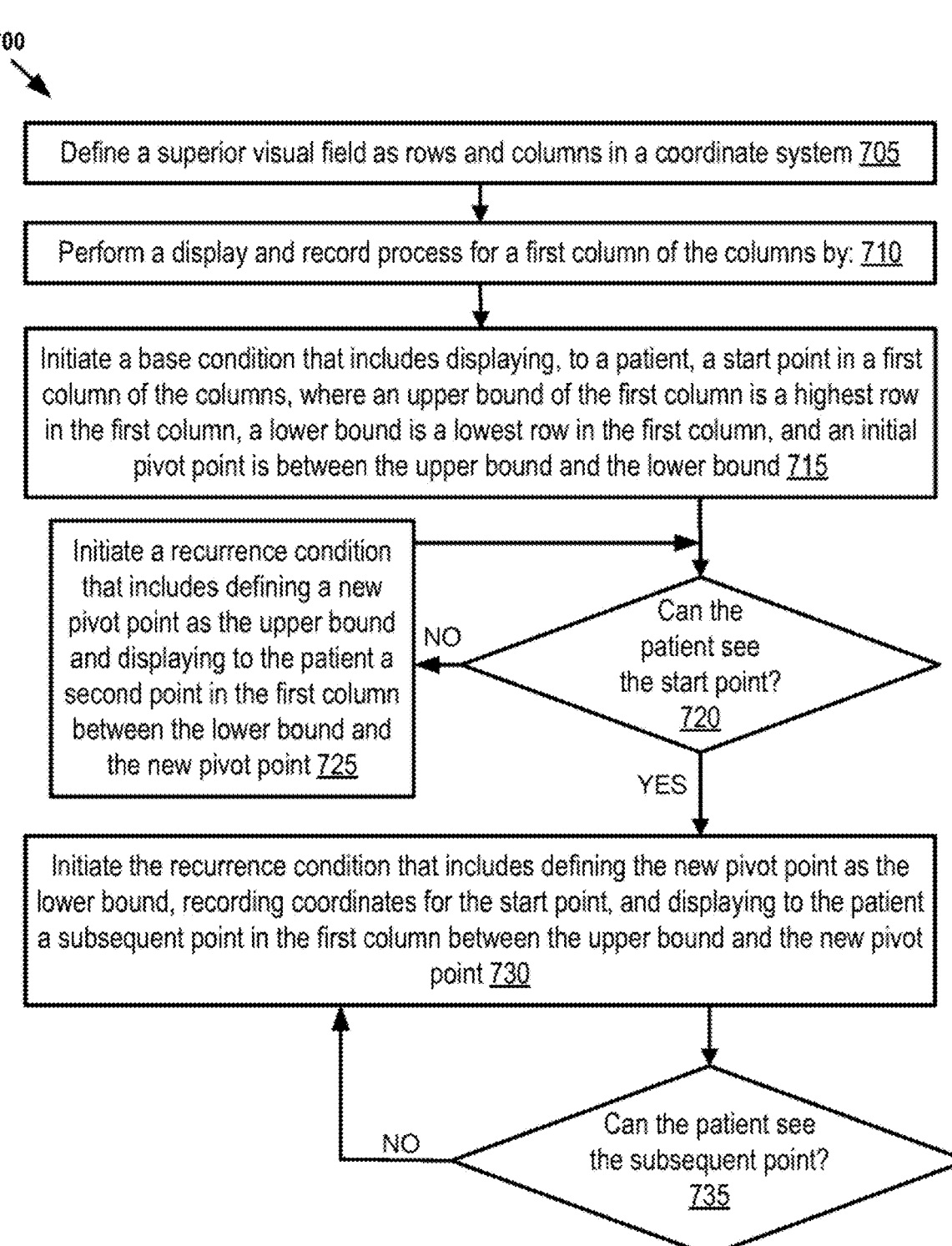

Define a superior visual field as rows and columns in a coordinate system 705

Perform a display and record process for a first column of the columns by: 710

Initiate a base condition that includes displaying, to a patient, a start point in a first column of the columns, where an upper bound of the first column is a highest row in the first column, a lower bound is a lowest row in the first column, and an initial pivot point is between the upper bound and the lower bound 715

Initiate a recurrence condition that includes defining a new pivot point as the upper bound and displaying to the patient a second point in the first column between the lower bound and the new pivot point 725

Can the patient see the start point? 720

NO

YES

Initiate the recurrence condition that includes defining the new pivot point as the lower bound, recording coordinates for the start point, and displaying to the patient a subsequent point in the first column between the upper bound and the new pivot point 730

Can the patient see the subsequent point? 735

NO

YES

Record coordinates for the subsequent point and continue with the recurrence condition 740

Initiate a stop condition when a difference between the new pivot point and a previous pivot point is less than a predetermined threshold 745

Repeat the display and record process for additional columns 750

900

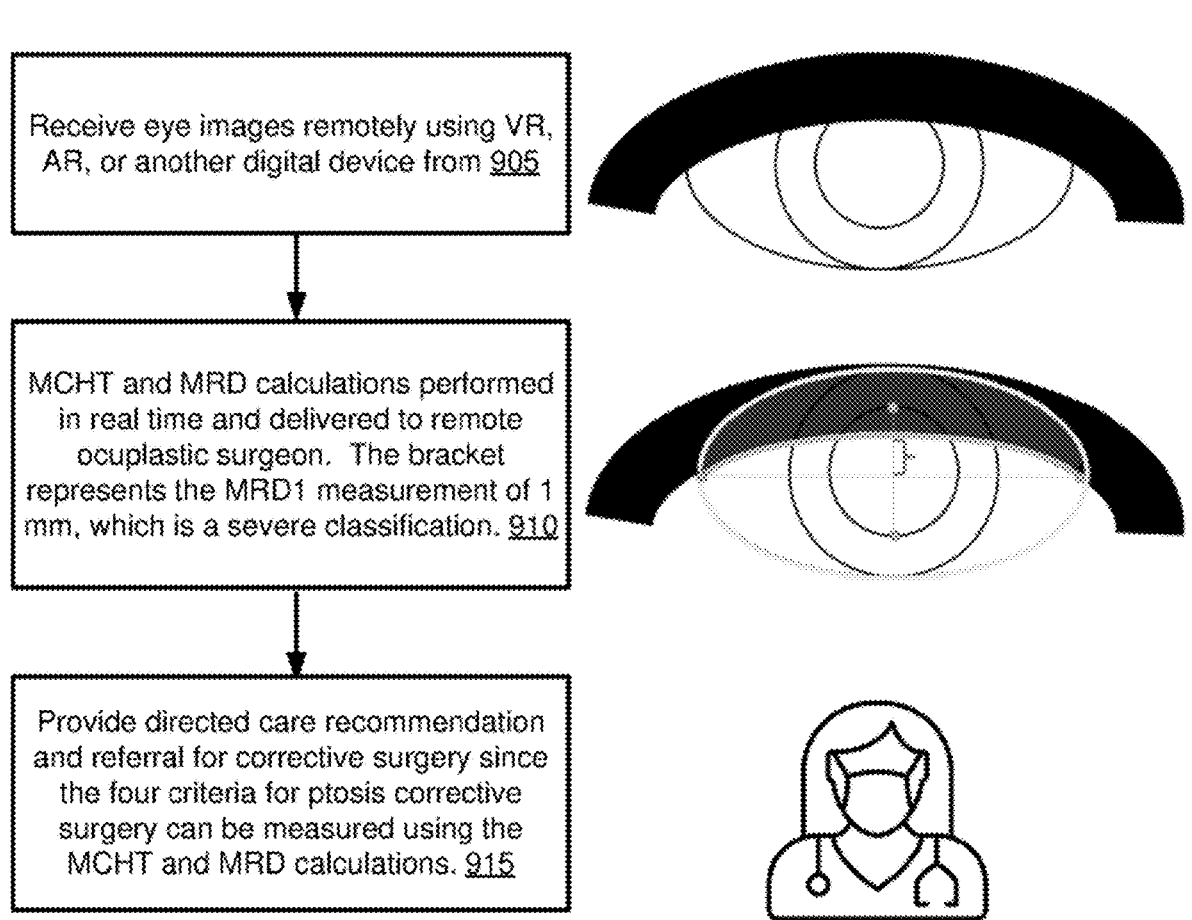

Receive eye images remotely using VR, AR, or another digital device from 905

MCHT and MRD calculations performed in real time and delivered to remote ocuplastic surgeon. The bracket represents the MRD1 measurement of 1 mm, which is a severe classification. 910

Provide directed care recommendation and referral for corrective surgery since the four criteria for ptosis corrective surgery can be measured using the MCHT and MRD calculations. 915

FIG 9

HEAD-MOUNTED SYSTEM FOR MEASURING PTOSIS

FIELD

The described embodiments relate generally to methods, systems, and non-transitory computer-readable media to predict a visual field loss of a patient due to medical conditions that cause impediments such as ptosis.

BACKGROUND

Blepharoptosis, or superior ptosis (henceforth referred to as "ptosis"), is a drooping of the upper eyelid that causes a low-lying upper eyelid margin, which can result in visual field deficits. Many cases are benign in etiology, but it can also serve as the first indication of emergent serious neurogenic conditions. The most common type of ptosis is aponeurotic, which results from overstretching of levator muscles due to factors such as aging. One estimate places the prevalence of aponeurotic ptosis at 15% of the general population, with a high correlation against greater than 65 years of age.

Ptosis interrupts patient quality of life in several ways, including increasing aged appearance and causing visual field obstructions. Corrective surgery for ptosis is possible through surgeries such as blepharoplasty, although specific severity and deficit measurements must be acquired by a physician in order to bill for reimbursement with US codes such as CPT 15823. Specifically, a physician must perform a visual field examination, such as perimetry, which can demonstrate that the patient would receive an improvement of 12° or 30% of the superior visual field (SVF) with a correction. This is done by performing a visual field exam at baseline with ptosis, and then once again with a taping of the ptotic eyelid to simulate a corrective surgery.

Visual field measurements can be tedious and are currently performed by methods that are either costly and time-consuming, or inaccurate. For the prior, physicians can utilize a Humphrey Visual Field Analyzer (HVFA), which can take 15-60 minutes when testing for both uncorrected and corrected SVF. Perimeters like the HVFA have demonstrated poor replicability within each patient due to factors such as patient fatigue and technician bias/error. Furthermore, these machines are expensive and require a certified technician. Therefore, oculoplastic surgeons often have to refer their patients to a general ophthalmologist to have these measurements performed, causing a delay in the surgery, as well as greater cost and burden to the patient. While other cheaper, faster strategies exist, such as the Tangent Screen Test, they are often very inaccurate and difficult to generate an output report that would be accepted by insurance.

Because of the inaccuracies associated with measuring SVF loss in ptosis patients with existing visual field measurement methods, oculoplastic surgeons often employ a measurement called margin to reflex distance (MRD), which is the distance between the center of the pupil and the upper eyelid directly above the pupil. MRD is useful in corroborating visual field measurements and binning ptosis patients into severity grades as follows: mild (MRD=3-4 mm), moderate (MRD=2-3 mm), and severe (MRD=<2 mm).

The use of virtual reality (VR) for visual function testing has recently become popular, with systems such as the PICO and HTC Vive Pro Eye demonstrating strong performance in accuracy and patient enjoyment as compared to standard ophthalmic technologies. Some groups have developed perimetry, and even SVF perimetry, on these platforms. However, these tests are mostly analogous to those performed on an HVFA, and therefore still take a substantial amount of time to complete. This is because they were not designed to be used in a highly specialized workflow, such as that of oculoplastic surgeons who prefer to make quick surgery "go-no go" decisions during the first consultation. Furthermore, none of the available VR testing modalities has attempted to adapt onboard technologies, such as eye tracking cameras, to assist physicians in MRD measurement.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In some embodiments, a computer-implemented method to predict visual field loss comprises defining a superior visual field as rows and columns in a coordinate system. A method to predict visual field loss includes defining a superior visual field as rows and columns in a coordinate system. The method further includes performing a display and record process for a first column of the columns by: initiating a base condition that includes displaying, to a patient, a start point in a first column of the columns, wherein an upper bound of the first column is a highest row in the first column, a lower bound is a lowest row in the first column, and an initial pivot point is between the upper bound and the lower bound, receiving input indicative of whether the start point is visible to the patient, initiating a recurrence condition where responsive to a determination that the patient can see the start point, defining a new pivot point as the lower bound, recording coordinates for the start point, and displaying to the patient a subsequent point in the first column between the upper bound and the new pivot point, receiving input indicative of whether the subsequent point is visible to the patient, responsive to the patient seeing the subsequent point, recording coordinates for the subsequent point and continuing with the recurrence condition, and initiating a stop condition when a difference between the new pivot point and a previous pivot point is less than a predetermined threshold. The method further includes repeating the display and record process for additional columns of the columns. The method further includes defining an eyelid meridian based on recorded coordinates for a set of points that are visible to the patient. The method further includes calculating an area of the superior visual field based on the eyelid meridian. The method further includes determining the visual field loss based the area of the superior visual field.

In some embodiments, the method further includes responsive to the patient not seeing the start point, defining the new pivot point as the upper bound and displaying to the patient a second point in the first column between the lower bound and the new pivot point and responsive to the patient seeing the second point, recording coordinates for the second point and continuing with the recurrence condition. In some embodiments, the method further includes after the stop condition is initiated, displaying an additional point above coordinates for the stop condition and an additional point below coordinates for the stop condition to confirm the stop condition. In some embodiments, the method further includes responsive to the patient not seeing one or more of the additional point above the coordinates for the stop condition and the additional point below the coordinates, returning to the recurrence condition until the stop condition is reached again. In some embodiments, the display and record process for the additional columns of the columns is performed to determine a first superior visual field with no ptosis when the eyelid is taped and a second superior visual field with ptosis when the eyelid is not taped. In some embodiments, the method further includes receiving eye images remotely, wherein the display and record process is performed based on the eye images and transmitting the recorded coordinates and the visual field loss to a remote oculoplastic surgeon. In some embodiments, displaying the start point is via a virtual reality (VR) headset or an augmented reality (AR) headset. In some embodiments, the VR headset includes a trigger pull that the patient can activate to provide the input that the patient saw the start point or an audio interface that records audio from the patient. In some embodiments, the coordinates for the set of points are automatically recorded by eye-tracking cameras. In some embodiments, the eye-tracking cameras include infrared (IR) cameras or near infrared (NIR) cameras. In some embodiments, the method further includes prior to defining the superior visual field: determining a margin to reflex distance (MRD) and Cartesian coordinates for an upper eyelid relative to a curvilinear arc of the upper eyelid and selecting a set of candidate points to be shown to the patient based on the MRD. In some embodiments, the method further includes generating a user interface that includes options to define one or more of: boundaries of a vertical axis, a horizontal axis, or a planar axis; a degree offset of each of the columns relative to tested points; x-axis and y-axis bounds; and the coordinate system as Cartesian, polar, spherical, or orthogonal curvilinear coordinates. In some embodiments, the visual field loss is used to assess eye health for one or more of a brain pathology, an ocular condition, or a musculoskeletal condition and wherein the recorded coordinates are combined with healthcare data analysis to identify when the patient is at higher risk of ptosis. In some embodiments, determining the visual field loss is based on a Ramanujan calculation to approximate a predicted field of an eyeball.

In some embodiments, a system to predict visual field loss comprises a processor and a memory coupled to the processor, with instructions stored thereon that, when executed by the processor, cause the processor to perform operations. The operations include defining a superior visual field as rows and columns in a coordinate system. The operations further include performing a display and record process for a first column of the columns by: initiating a base condition that includes displaying, to a patient, a start point in a first column of the columns, wherein an upper bound of the first column is a highest row in the first column, a lower bound is a lowest row in the first column, and an initial pivot point is between the upper bound and the lower bound, receiving input indicative of whether the start point is visible to the patient, initiating a recurrence condition where responsive to a determination that the patient can see the start point, defining a new pivot point as the lower bound, recording coordinates for the start point, and displaying to the patient a subsequent point in the first column between the upper bound and the new pivot point, receiving input indicative of whether the subsequent point is visible to the patient, responsive to the patient seeing the subsequent point, recording coordinates for the subsequent point and continuing with the recurrence condition, and initiating a stop condition when a difference between the new pivot point and a previous pivot point is less than a predetermined threshold. The operations further include repeating the display and record process for additional columns of the columns. The operations further include defining an eyelid meridian based on recorded coordinates for a set of points that are visible to the patient. The operations further include calculating an area of the superior visual field based on the eyelid meridian. The operations further include determining the visual field loss based the area of the superior visual field.

In some embodiments, the system further includes a display and one or more eye-tracking cameras, wherein the system is a virtual reality headset or an augmented reality headset. In some embodiments, the operations further include: responsive to the patient not seeing the start point, defining the new pivot point as the upper bound and displaying to the patient a second point in the first column between the lower bound and the new pivot point and responsive to the patient seeing the second point, recording coordinates for the second point and continuing with the recurrence condition. In some embodiments, the operations further include after the stop condition is initiated, displaying an additional point above coordinates for the stop condition and an additional point below coordinates for the stop condition to confirm the stop condition.

In some embodiments, a non-transitory computer-readable medium with instructions stored thereon to predict visual field loss that, when executed by one or more computers, cause the one or more computers to perform operations. The operations include defining a superior visual field as rows and columns in a coordinate system. The operations further include performing a display and record process for a first column of the columns by: initiating a base condition that includes displaying, to a patient, a start point in a first column of the columns, wherein an upper bound of the first column is a highest row in the first column, a lower bound is a lowest row in the first column, and an initial pivot point is between the upper bound and the lower bound, receiving input indicative of whether the start point is visible to the patient, initiating a recurrence condition where responsive to a determination that the patient can see the start point, defining a new pivot point as the lower bound, recording coordinates for the start point, and displaying to the patient a subsequent point in the first column between the upper bound and the new pivot point, receiving input indicative of whether the subsequent point is visible to the patient, responsive to the patient seeing the subsequent point, recording coordinates for the subsequent point and continuing with the recurrence condition, and initiating a stop condition when a difference between the new pivot point and a previous pivot point is less than a predetermined threshold. The operations further include repeating the display and record process for additional columns of the columns. The operations further include defining an eyelid meridian based on recorded coordinates for a set of points that are visible to the patient. The operations further include calculating an area of the superior visual field based on the eyelid meridian. The operations further include determining the visual field loss based the area of the superior visual field.

In some embodiments, the operations further include responsive to the patient not seeing the start point, defining the new pivot point as the upper bound and displaying to the patient a second point in the first column between the lower bound and the new pivot point and responsive to the patient seeing the second point, recording coordinates for the second point and continuing with the recurrence condition.

As a result, this application proposes novel methods of measuring ptosis through head-mounted systems that can improve the decision-making process in specialized practices, such as those of oculoplastic surgeons. However, this also introduces a unique tele-ophthalmology opportunity, where primary care or rural healthcare practices can perform a detailed visual field analysis with MRD outside of vision specialist practices. These readouts can be sent to specialists for remote decision-making on corrective surgeries, reducing the time-to-operation and minimizing burdens on specialists and patients.

BRIEF DESCRIPTION OF THE DRAWING

The disclosure is illustrated by way of example, and not by way of limitation, in the accompanying drawings in which like reference numerals are used to refer to similar elements.

FIGS. 7A-B illustrates a telemedicine flowchart for ptosis patients, according to some embodiments.

FIG. 9 illustrates an example flowchart for calculating MCHT, according to some embodiments.

DETAILED DESCRIPTION

Figure 1:
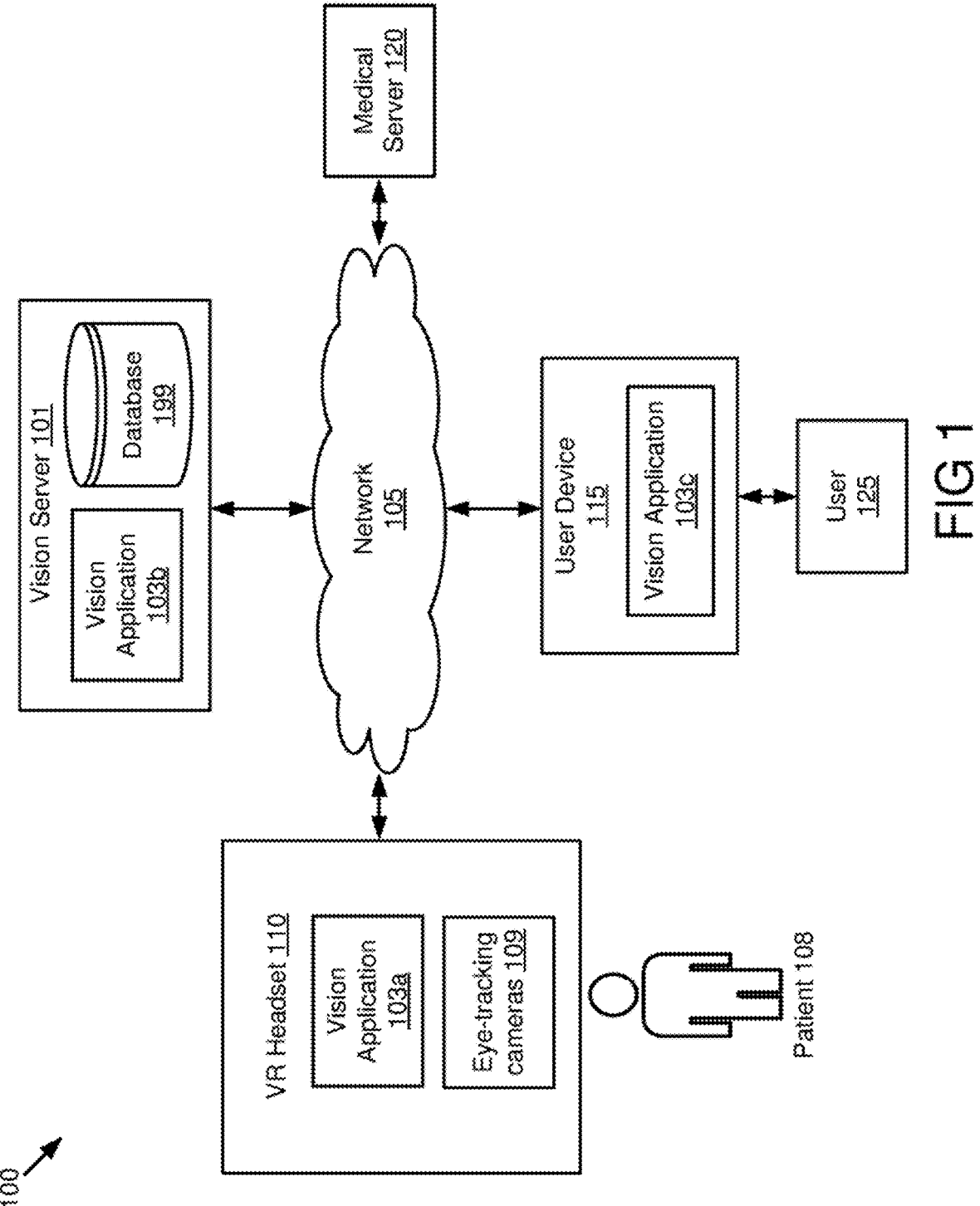
FIG. 1 illustrates an operating environment that determines a percentage of visual field loss of an eye, according to some embodiments.

There does not currently exist a strategy by which physicians, particularly oculoplastic surgeons, can measure both superior visual field (SVF) and margin to reflex distance (MRD) within a single technology in a rapid, consistent, and affordable manner. A technological approach beneficial to the field of oculoplastics would embody software embedded within a portable system, such as a head-mounted virtual reality (VR) headset, that also has anterior chamber imaging capabilities, such as through eye tracking cameras. This system could also utilize onboard processing capabilities, or connection to a portable computer, in order to provide real-time modifications to the visual field test that can accelerate the test based on data from imaging or patient background.

VR headsets hold high potential for specialized ptosis-measuring use in specialized oculoplastic workflows due to their constantly increasing screen sizes (to assess a greater percentage of the visual field), and their embedded eye-tracking cameras that can provide a frontal view of the eyes and eyelids. Head-mounted, modular ophthalmic systems also hold potential because of their ability to overlap data from prior modules (i.e. retinal imaging) onto the module currently in use (i.e. VR for visual function testing), which can provide the same benefits as a VR headset, but additionally accelerate visual field examinations by predicting which visual field stimuli are unnecessary to present to the patient. In order to maximize the granularity of ptosis measurement, we propose 1) algorithmic adaptation of existing VR headsets for ptosis measurement with a Median Cut Hemifield Test (MCHT) algorithm, and 2) adaptation of modular head-mounted systems. We further propose the use of eye tracking cameras to predict the natural surface area of a patient's eye through contralateral referencing, which can then approximate superior view field (SVF) impediments on the ptosis-impacted (ipsilateral) eye by analyzing eyelid surface area. We further propose a method of real-time adjustment of stimulus presentation to the patient based on eye tracking predictions in order to reduce testing time without sacrificing accuracy.

Isolated use of any perimetry device has the potential for lower replicability and reliability within each patient than when one consistently corroborates perimetry outputs with secondary measures, such as MRD. This is crucial, as it increases the likelihood of helping those who actually need corrective surgery to receive it, while also assisting those with mild ptosis from avoiding what is likely an unnecessary operation. There exists no prior art for the use of eye tracking cameras, particularly infrared cameras, within VR headsets to identify the bounds of a person's healthy, contralateral eyelid and predict the level of droop and visual field interruption in the ipsilateral, ptotic eyelid. For this step, the center of the pupil is considered the center of the visual field and center of the anterior portion of the eye relative to the orbit, serving as a predictive anchor point. The perimeter of the eye is then approximated by measuring the curvature of the visible sclera and using a Ramanujan calculation to artificially complete and approximate an ellipse and calculate the two-dimensional surface area. The bounds of the upper eyelid are then calculated by conventional infrared mapping and converting the lower lid to Cartesian coordinates and calculating the area underneath using the Trapezoidal Rule. The contralateral circle and eyelid are then overlaid on the diseased eye and the bounds of the ptotic eyelid are also selected. An MRD is then calculated between the center of the pupil and both eyelid overlays to predict the percent visual field loss. This quantification method enables vision specialists to obtain measurements of the eyelid with respect to the pupil, inferior (contralateral vs. ipsilateral superior) eyelid, and other anatomical markers in conjunction with eye tracking.

The MRD calculation method can be used for increasing the efficiency of the MCHT in real-time, as well as for increasing the output accuracy of each test. The Cartesian coordinates of the upper eyelid can bound the space of points relative to the curvilinear arc to increase precision of the meridian and reduce time for its localization.

When using a VR headset with dual-integrated or interchangeable imaging and VR capabilities, such as a modular system, data from a previous module can be used to even further inform MCHTs. This demonstrates the benefits of a modular ophthalmic system, as one can make tests more efficient through utilization of extraocular (eye tracking analysis of eyelid structure) and intraocular (retinal imaging analysis) data.

Ptosis perimetry tests aim to assess changes in the superior aspect of the visual field and determine whether a patient is a candidate for surgical intervention. Existing approaches, such as the Humphrey Visual Field Analyzer, broadly evaluate alterations in the visual field and are not specific for ptosis. While Humphrey technologies have superior visual field settings, they still take a substantial amount of time, and Humphrey-mediated automated static perimetry has been shown to be less sensitive for ptosis visual fields. The MCHT algorithm, is a scalable alternative that optimizes assessment at the superior visual field, thereby dramatically decreasing the time required for evaluation and possibly increasing accuracy of measurements.

The MCHT is a recursive algorithm that incrementally maps out a meridian in the superior aspect of the visual field. The base case assigns a pivot as the median point in the visual field or a prior pivot if one exists. Each subsequent recursion step re-assigns the pivot based on whether the pivot is observed by the user: if the pivot is observable, the new pivot is set as the median between the current pivot and the uppermost aspect of the visual field, otherwise the new pivot is set as the median between the current point and lowermost aspect of the visual field. The stop condition is triggered when the old and new pivots differ by a predetermined threshold. In some embodiments the predetermined threshold is 10 or fewer pixels. In other embodiments, the predetermined threshold is adaptive. This threshold can be adjusted if the provider deems appropriate. This process is repeated for every vertical span n degrees along the meridian and is run twice, with and without taping the user's eyelids. The user's superior visual field is calculated as the area under the meridian via the integration for area under the curve (AUC) or similar integration approximation techniques (e.g., the Trapezoidal rule) and a percent difference is calculated to quantify the level of ptosis. For users with ptosis (drooping eyelid), taping the eyelids simulates a condition where the drooping eyelid conditions is temporarily removed, thus providing a higher SVF (that is also indicative of potential improvement in the vision post-surgery for ptosis). The condition without taping the eyelids provides measurements of the user's current vision condition.

Operating Environment 100

FIG. 1 illustrates a block diagram of an example environment 100. In some embodiments, the environment 100 includes a vision server 101, a user device 115, a virtual reality (VR) headset 110, a medical server 120, and a network 105. A user 125 may be associated with the user device 115 and a patient 108 may be associated with the VR headset 110. In some embodiments, the environment 100 may include other servers or devices not shown in FIG. 1 and the vision server 101 server, the user device 115, or the medical server 120 may not be included. In FIG. 1 and the remaining figures, a letter after a reference number, e.g., "103a," represents a reference to the element having that particular reference number. A reference number in the text without a following letter, e.g., "103," represents a general reference to embodiments of the element bearing that reference number.

The VR headset 110 may be physical hardware that fits on the head of patient 108 head and is equipped with one or more eye-tracking cameras 109. In some embodiments, the VR headset 110 include a processor, a memory, and network communication hardware. In some embodiments, the headset is a head-mounted system, such as a modular system or a modular headset. Examples of a modular headset with VR capabilities are described in PCT application No. PCT/US21/27544 filed on Apr. 15, 2021 and entitled "Modular Platform for Ocular Evaluations," the entirety of which is herein incorporated by reference. Other VR headsets 110 may be used.

In some embodiments, the eye-tracking cameras 109 include infrared (IR) or near infrared (NIR) cameras that communicate with the processor of the VR headset 110. In some embodiments, the IR cameras or NIR cameras emit IR light. When the IR light falls on a patient's 108 cornea, part of the light is reflected towards the light source and a glint appears on the patient's 108 eye. A distance between the glint and the center of the patient's 108 pupil increases as the patient 108 looks away from the light source. In some embodiments, the IR or NIR cameras capture an image of a dark pupil and an image of a bright pupil and the processor determines a difference between the images in order to identify a gaze of each eye, gaze point, eye openness, etc.

In some embodiments, the modular head-mounted system may include retinal imaging or anterior chamber imaging data that enhances perimetry accuracy of the MCHT. The modular head-mounted system may reduce presented visual field stimuli presented to a patient 108 based on healthy areas of the retina for accelerated testing, prioritize presentation of visual field stimuli presented to a patient that overlaps with diseased portions of the retina, and/or adapt to visual field stimuli presented to a patient based on anterior chamber abnormalities, such as cataracts, corneal abrasions, or external factors such as ptotic eyelids.

In some embodiments, when the eye-tracking cameras 109 include IR cameras or NIR cameras, the images may be captured in a dark environment. As a result of the dark environment, the patient's 108 pupils experience less pupil diameter variation as the MRD camera measurements are being taken. In addition, the IR cameras or NIR cameras create less of a distraction than a visible light-dependent camera while the MCHT is performed.

The VR headset 110 includes a display that displays graphical information to the patient 108 and tracks the patient's 108 response to the graphical information. In some embodiments, the eye-tracking cameras 109 capture images of the patient's 108 eyes as the graphical information is displayed. In some embodiments, the eye-tracking cameras 109 collect images of the anterior portion of the patient's eye and eyelids.

The VR headset 110 may display points on the display to the patient 108 and request the patient 108 to acknowledge whether the patient 108 can see the points. For example, the VR headset 110 may include a trigger pull or other interface on a VR headset controller with a mechanism for providing indications, such as a button that the patient 108 can press or activate when the patient 108 sees a point. In another example, the VR headset 110 may include an audio interface with a microphone that records a patient's 108 response to seeing the points, such as by stating "seen" or "unseen" to indicate that the patient has seen or not seen the point.

The VR headset 110 may record coordinates for the points that are visible to the patient 108, based on the indications provided by the patient. The VR headset 110 may include network capabilities for transmitting the coordinates for the points indicated as visible or not visible to a vision application 103 that is stored and/or executed on the vision server 101 and/or the user device 115.

In some embodiments, the VR headset 110 includes a vision application 103a that provides the graphical data that is displayed to a patient 108. In some embodiments, the vision application 103a on the headset 110 performs all the vision analysis and transmits the results to another entity in the environment 100, such as the user device 115, the vision server 101, or the medical server 120. In some embodiments, the vision application 103a receives instructions from a vision application 103 stored on another entity, such as the vision application 103b stored on the vision server 101. As a result, descriptions of the vision application 103 may all be performed on one entity or broken up into multiple entities in the environment 100.

The vision application 103a may include eye tracking software that uses anatomical markers, such as pupil center corneal reflection, gaze data, pupil diameter, pupil contour, and other markers not denoted here, to determine relative Cartesian coordinates for the eyelid all after simple nine-point calibration for eye tracking is performed.

The vision application 103a may include code and routines operable to predict a percentage of visual field loss. In some embodiments, the vision application 103a communicates with a VR headset 110 to obtain images of the patient's 108 eyes, coordinates for a set of points that are visible to the patient 108 when the set of points are displayed on the VR headset 110 to the patient, etc. In some embodiments, the vision application 103a applies a MCHT to determine a percentage of visual field loss. In some embodiments, the vision application 103a calculates a margin to reflex distance (MRD) to improve the efficiency of the MCHT.

In some embodiments, the vision application 103a may be implemented using hardware including a central processing unit (CPU), a field-programmable gate array (FPGA), an application-specific integrated circuit (ASIC), any other type of processor, or a combination thereof. In some embodiments, the vision application 103a may be implemented using a combination of hardware and software.

In some embodiments, the VR headset 110 includes augmented reality (AR) capabilities as well. For example, the display may be translucent and show the user information within the room, while displaying a set of points for performing the MCHT as an overlay. In other examples, separate AR hardware may be used to implement the MCHT, such as glasses that implement the MCHT.

The vision server 101 may include a processor, a memory, and network communication hardware. In some embodiments, the vision server 101 is a hardware server. The vision server 101 is communicatively coupled to the network 105 via a wired connection, such as Ethernet, coaxial cable, fiber-optic cable, etc., or a wireless connection, such as Wi-Fi®, Bluetooth®, or other wireless technology. In some embodiments, the vision server 101 sends and receives data to and from one or more of the user devices 115, the VR headset 110, and the medical server 120. The vision server 101 may include a vision application 103b and a database 199. The vision application 103b may perform some or all of the steps described above with reference to the vision application 103a.

The database 199 may store medical information associated with patients 108, including the images of a patient's eyes 108, coordinates for a set of points that are visible to the patient 108, the patient's history 108, medical recommendations, etc. Storing and processing of medical information is in compliance with applicable laws and regulations.

The user device 115 may be a computing device that includes a memory and a hardware processor. For example, the user device 115 may include a desktop computer, a laptop, a desktop computer, a workstation, a smartphone, a mobile device, a tablet computer, a mobile telephone, a mobile email device, or another electronic device capable of accessing a network 105. The user device 115 may include a vision application 103b that performs the functions of the vision application 103a described above that is stored on the vision server 101.

The medical server 120 may be associated with different types of medical treatment. For example, the medical server 120 may be associated with a surgeon that performs corrective surgery for ptosis, such as an oculoplastic surgeon. Because surgeons can receive the relevant information over a network 105, the surgeons can make remote decisions on corrective surgeries, thereby reducing the time-to-operation and minimizing burdens on specialists and patients 108.

The medical server 120 includes a processor, a memory, and network communication hardware. In some embodiments, the medical server 120 is a hardware server. In some embodiments, the vision application 103 may transmit information to a medical server 120, such as a prediction of a percentage of visual field loss, along with the information used to make the prediction and the calculations used to make the prediction. In some embodiments, the medical server 120 includes an interface for providing remote treatment to the patient, such as remote robotic surgery (e.g., a DaVinci Robot).

Computing Device Example 200

Figure 2:
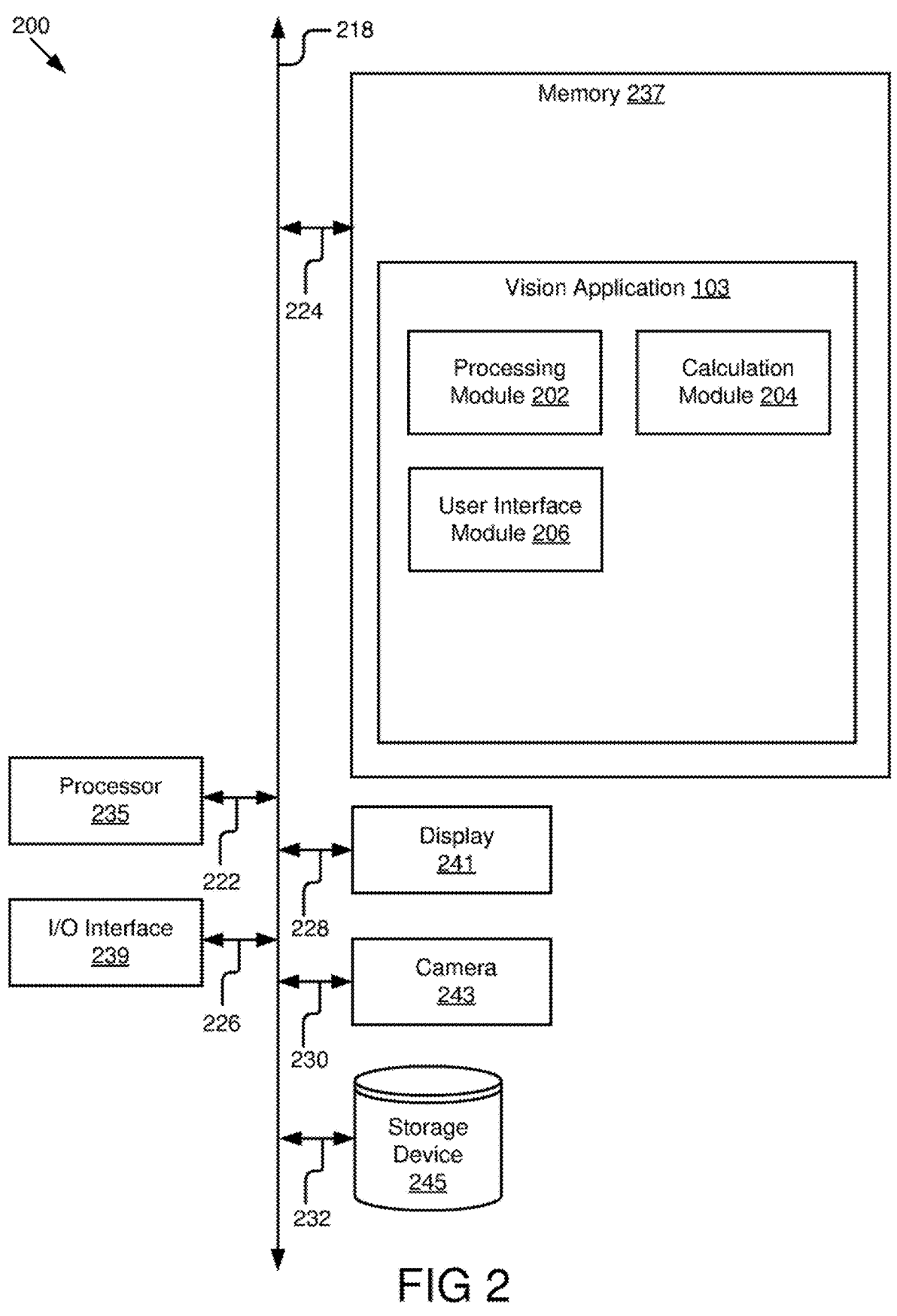
FIG. 2 illustrates a computing device that determines a percentage of visual field loss of an eye, according to some embodiments.

FIG. 2 is a block diagram of an example computing device 200 that may be used to implement one or more features described herein. The computing device 200 can be any suitable computer system, server, or other electronic or hardware device. In one example, the computing device 200 is the vision server 101 used to implement the vision application 103a. In another example, the computing device 200 is the user device 115 or VR headset 110 used to implement the vision application 103b. In yet another example, the vision application 103 is in part on the user device 115 or VR headset 110 and in part on the vision server 101.

One or more methods described herein can be run in a standalone program that can be executed on any type of computing device, a program run on a web browser, a mobile application ("app") run on a mobile computing device (e.g., cell phone, smart phone, smart display, tablet computer, laptop computer, etc.).

In some embodiments, computing device 200 includes a processor 235, a memory 237, a I/O interface 239, a display 241, a camera 243, a storage device 245, and a bus 218. The processor 235 may be coupled to a bus 218 via signal line 222, the memory 237 may be coupled to the bus 218 via signal line 224, the I/O interface 239 may be coupled to the bus 218 via signal line 226, the display 241 may be coupled to the bus 218 via signal line 228, the camera 243 may be coupled to the bus 218 via signal line 230, and the storage device 245 may be coupled to the bus 218 via signal line 232. Bus 218 enables data communication between the different components coupled to the bus 218.

Processor 235 can be one or more processors and/or processing circuits to execute program code and control basic operations of the computing device 200. A "processor" includes any suitable hardware system, mechanism or component that processes data, signals or other information. A processor may include a system with a general-purpose central processing unit (CPU) with one or more cores (e.g., in a single-core, dual-core, or multi-core configuration), multiple processing units (e.g., in a multiprocessor configuration), a graphics processing unit (GPU), a field-programmable gate array (FPGA), an application-specific integrated circuit (ASIC), a complex programmable logic device (CPLD), dedicated circuitry for achieving functionality, a special-purpose processor to implement neural network model-based processing, neural circuits, processors optimized for matrix computations (e.g., matrix multiplication), or other systems. In some embodiments, processor 235 may include one or more co-processors that implement neural-network processing. In some embodiments, processor 235 may be a processor that processes data to produce probabilistic output, e.g., the output produced by processor 235 may be imprecise or may be accurate within a range from an expected output. Processing need not be limited to a particular geographic location or have temporal limitations. For example, a processor may perform its functions in real-time, offline, in a batch mode, etc. Portions of processing may be performed at different times and at different locations, by different (or the same) processing systems. A computer may be any processor in communication with a memory.

Memory 237 is typically provided in computing device 200 for access by the processor 235, and may be any suitable processor-readable storage medium, such as random access memory (RAM), read-only memory (ROM), Electrical Erasable Read-only Memory (EEPROM), Flash memory, etc., suitable for storing instructions for execution by the processor or sets of processors, and located separate from processor 235 and/or integrated therewith. Memory 237 can store software operating on the computing device 200 by the processor 235, including a media application 103.

I/O interface 239 can provide functions to enable interfacing the computing device 200 with other systems and devices. Interfaced devices can be included as part of the computing device 200 or can be separate and communicate with the computing device 200. For example, network communication devices, storage devices (e.g., memory 237 and/or storage device 245), and input/output devices can communicate via I/O interface 239. In some embodiments, the I/O interface 239 can connect to interface devices such as input devices (keyboard, pointing device, touchscreen, microphone, camera, scanner, sensors, etc.) and/or output devices (display devices, speaker devices, printers, monitors, etc.).

Some examples of interfaced devices that can connect to I/O interface 239 can include a display 241 that can be used to display content, e.g., images, video, and/or a user interface of an output application as described herein, and to receive touch (or gesture) input from a user. For example, display 241 may be utilized to display a user interface that includes a subset of clusters of media items. Display 241 can include any suitable display device such as a liquid crystal display (LCD), light emitting diode (LED), or plasma display screen, cathode ray tube (CRT), television, monitor, touchscreen, three-dimensional display screen, or other visual display device. In some embodiments, the display 241 includes a brightness of greater than 300 nits, any resolution display, and a field of view (FOV) of greater than 45 degrees per eye. In some implementations, display 241 may include virtual reality display hardware such as lenses or other hardware. For example, display 241 can be a flat display screen provided on a mobile device, multiple display screens embedded in a glasses form factor or headset device, or a monitor screen for a computer device.

Camera 243 may be any type of image capture device that can capture images and/or video. In some embodiments, the camera 243 captures images or video that the I/O interface 239 transmits to the media application 103. In some embodiments, instead of using a VR headset 110 to capture information about the coordinates for points that are visible to a patient 108, in some embodiments, the computing device 200 includes an eye-tracking camera 243 that captures information about the coordinates for points that are visible to a patient 108.

The storage device 245 stores data related to the vision application 103. For example, the storage device 245 may store including the images of a patient's eyes 108, coordinates for a set of points that are visible to the patient 108, the patient's history 108, medical recommendations, etc. In embodiments where the vision application 103 is part of the vision server 101, the storage device 245 is the same as the database 199 in FIG. 1.

Example Vision Application 103

FIG. 2 illustrates an example vision application 103 that includes a processing module 202, a calculation module 204, and a user interface module 206.

The processing module 202 processes information about a patient's eye. In some embodiments, the processing module 202 includes a set of instructions executable by the processor 235 to process the information about the patient's eye. In some embodiments, the processing module 202 is stored in the memory 237 of the computing device 200 and can be accessible and executable by the processor 235.

In some embodiments, the processing module 202 receives information from a VR headset 110. For example, the processing module 202 may receive images of the patient's eye as recorded by an eye-tracking camera that is part of the VR headset 110 and coordinates for a set of points that are visible to the patient that is used by the calculating module 204 to apply the MCHT. In another example, the processing module 202 receives images of the eye from the VR headset 110 that are used by the calculating module 204 to determine the MRD. In yet another example, the processing module 202 receives the images of the eye and/or coordinates for a set of points that are visible to the patient from the camera 243 via the I/O interface 239.

The calculation module 204 performs vision calculations. In some embodiments, the calculation module 204 includes a set of instructions executable by the processor 235 to perform vision calculations. In some embodiments, the calculation module 204 is stored in the memory 237 of the computing device 200 and can be accessible and executable by the processor 235.

In some embodiments, the calculation module 204 applies a MCHT to the information received from the processing module 202. The MCHT may be a two-dimensional algorithm that runs in O(log-n) time that uses a binary search pattern for point generation of points to display to a patient. In some embodiments, the coordinates for the points that are displayed to the patient are associated with Cartesian coordinates. In other embodiments, the coordinates for the points are non-Cartesian coordinates, such as polar coordinates, spherical coordinates, orthogonal curvilinear coordinates, etc. The calculation module 204 may apply the MCHT using Cartesian coordinates or non-Cartesian coordinates.

Figure 3:
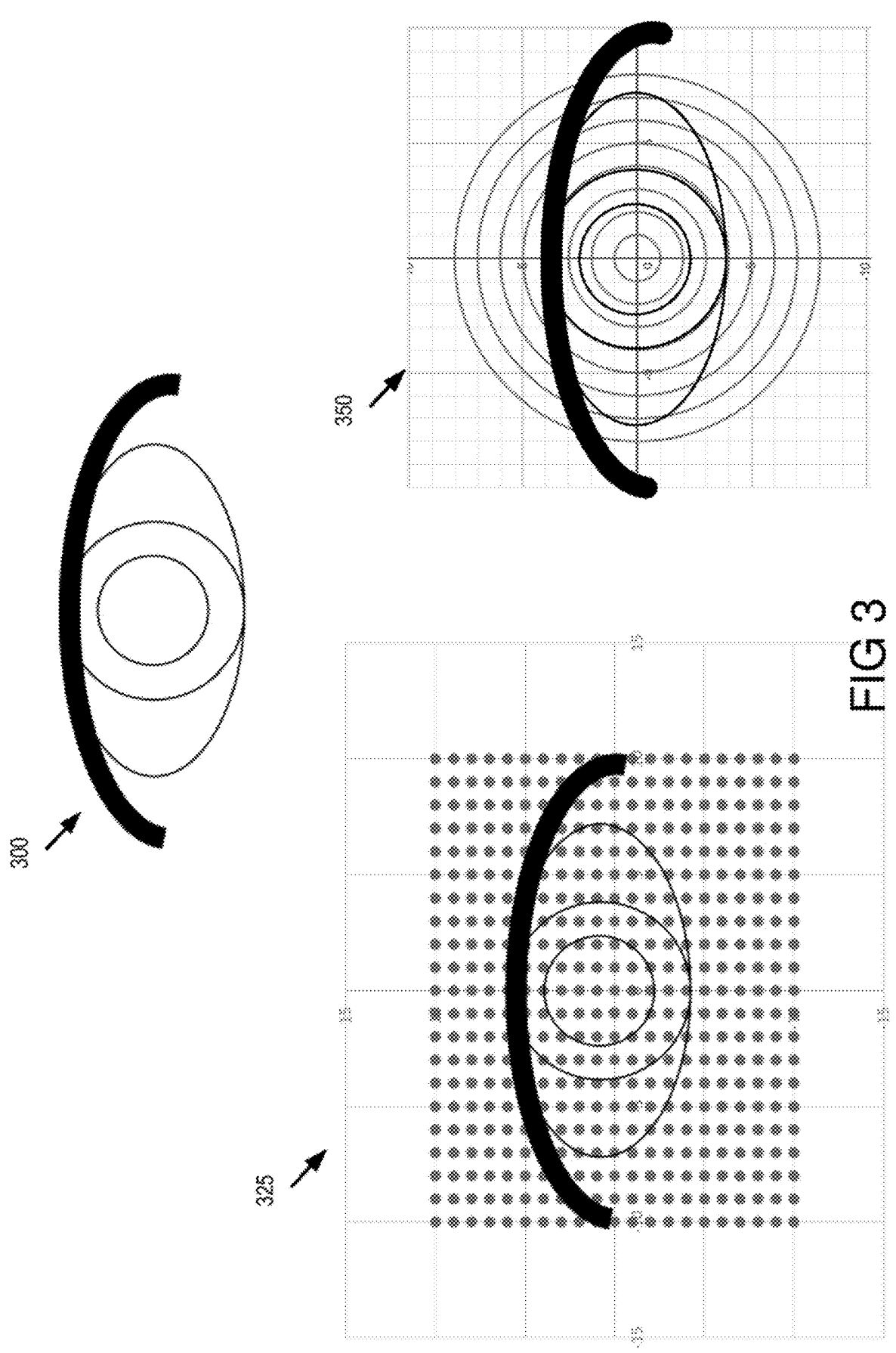
FIG. 3 illustrates different visualizations of a patient's eye, according to some embodiments.

Turning to FIG. 3, an eye 300 of a patient is illustrated. The eye may be represented in different types of coordinate systems. For example, the coordinate system can be Cartesian, polar, spherical, or orthogonal curvilinear coordinates. FIG. 3 illustrates a Cartesian grid 325 populated with superposition of a patient's eye. FIG. 3 also includes a polar grid 350 populated with superposition of a patient's eye.

The calculation module 204 defines rows and columns in a coordinate system, such as a Cartesian coordinate system, and determines where to display a start point in the coordinate system. In some embodiments, the calculation module 204 randomly determines where to display a start point. In some embodiments, the calculation module 204 starts in a middle of the coordinate system. In some embodiments, a user defines the starting point.

Figure 4:
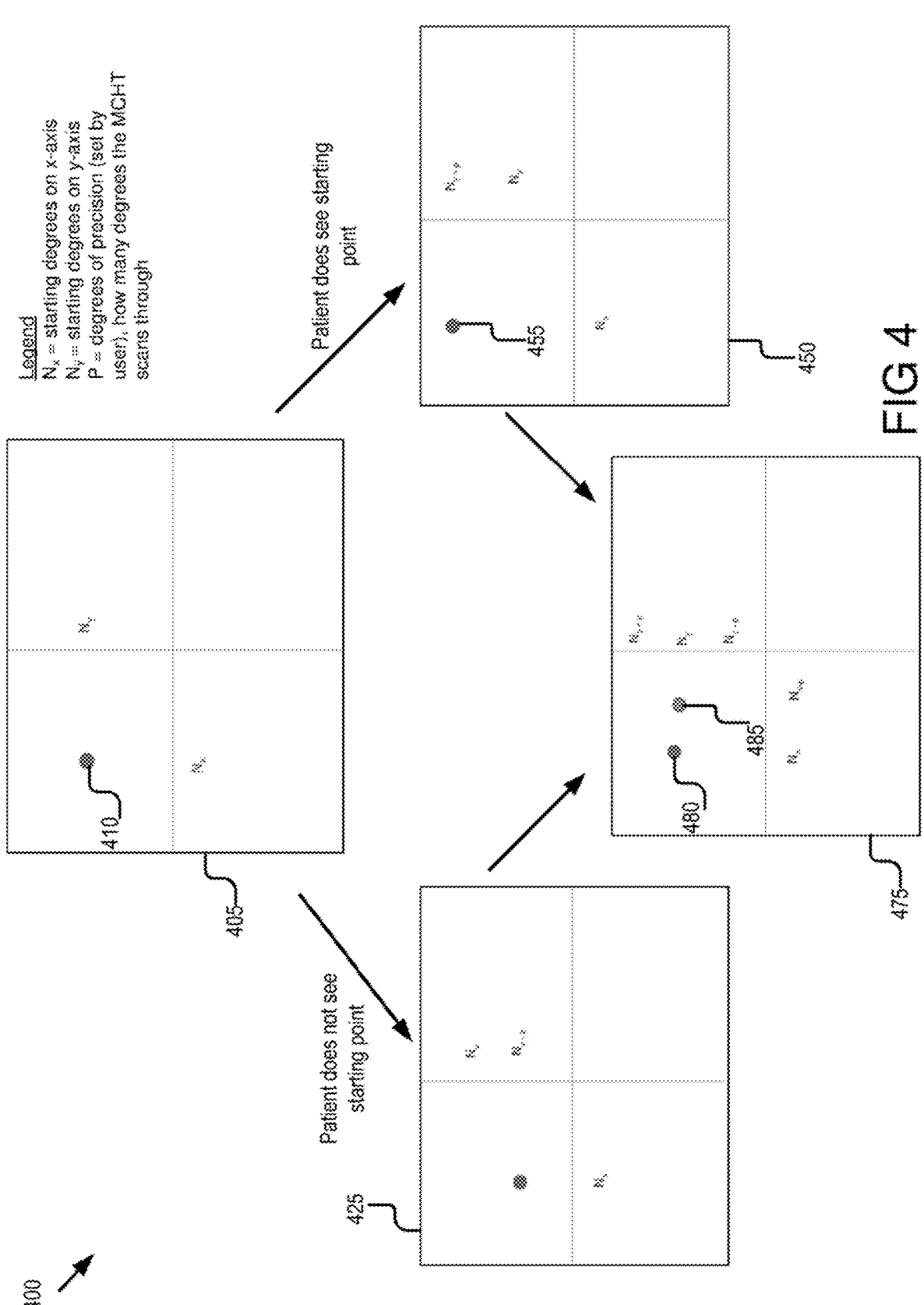
FIG. 4 illustrates a MCHT stimulus presentation process, according to some embodiments.

Turning to FIG. 4, an example 400 MCHT stimulus presentation process for a first column is illustrated. In this example, a starting point 410 is defined in the coordinate system 405 for the MCHT stimulus presentation process. Nx represents the starting degree on the x-axis and Ny represents the starting degree on the y-axis.

It is determined whether a patient can see the starting point 410. For example, the patient may provide physical input via a trigger pull, audio input via an audio interface, lack of any response to indicate that the starting point 410 was not visible, a reaction determined by an eye-tracking camera, etc. In some embodiments, the display with the coordinate system 405 and the starting point 410 also includes text or an auditory prompt asking the patient to confirm when they can view the starting point 410. In some embodiments, the display shows the starting point 410 for a predetermined amount of time (e.g., 1.25 seconds, five seconds, 10 seconds, etc.) before receiving confirmation from the patient that the starting point 410 is visible or the calculation module 204 determines that the patient cannot see the starting point 410. If the starting point 410 is visible to the patient, the calculation module 204 records the coordinates for the starting point 410.

If the patient cannot see starting point, the process moves to coordinate system 425 where a second point 430 is displayed with the same Nx, but the Ny is reduced to Ny–p (where "p" represents the precision). In some embodiments, an adapted binary search algorithm that defines the Ny–p as halfway between the last tested point (in this case the starting point 410) and a lowest row of the rows. Thus, the second point is lower and subsequent points are displayed as increasingly lower until the patient can see a subsequent point.

It is determined whether the patient can view the second point, for example, using the methods described above. If the patient can view the second point, the coordinate system 425 displays to the patient a third point half-way between a highest row of the rows and the second point. If the patient cannot view the second point, the coordinate system 425 displays to the patient a third point half-way between a lowest row of the rows and the second point. This process continues until a stop condition is reached. Then the coordinate system displays the coordinate system 475.

If the patient can see starting point, the process moves to coordinate system 450 where a subsequent point 455 is displayed with the same Nx, but the Ny is increased to Ny+p (where "p" represents the precision). In some embodiments, the Ny+p is halfway between the last tested point (in this case the starting point 410) and a highest row of the rows. Thus, the subsequent point is higher and additional points are displayed as increasingly higher until the patient cannot see an additional point. This process continues until a stop condition is reached and then the coordinate system 475 for the stop condition is displayed.

Coordinate system 475 illustrates a callback point to the original Starting Point Coordinates 480 to allow for users to retest the starting point. If the patient's answers contradict the first decision tree, then a new decision tree can be started.

Coordinate system 475 includes a next point 485 that is shown after the callback points are finished and Ny=0 or a maximum degree to scan across the x-axis. The maximum degree may be set by a user. The next point 485 is at Nx-p and Ny where a new column is tested. Additional columns can be tested, where each column is at a different position along the x-axis.

In some embodiments, the entire sequence is repeated for the new column and subsequent columns until the callback points are finished for all columns. In some embodiments, the process is performed twice: once when the patient's eye is taped (or otherwise the eyelid is kept open/prevented from drooping) and once when the patient's eye is untaped. Taping is performed in order to simulate the impact of a surgical correction on a patient's observable superior visual field. In some embodiments, the calculation module 204 presents the results for both a taped and untaped eye. In some embodiments, where the calculation module 204 determines that one of the points is an outlier (e.g., a point exceeds a threshold difference in the y-axis from the other points or an average of the other points), the calculation module 204 discards the point. The calculation module 204 may retest the patient with that point.

In some embodiments, the calculation module 204 determines the user's superior visual field as the area under the meridian via integration for area under the curve (AUC) or similar integration approximation techniques (e.g. Trapezoidal rule) and a percent difference is calculated to quantify the level of ptosis. In some embodiments, the calculation module 204 uses a Ramanujan calculation to approximate a predicted field of the eyeball by calculating a perimeter of an ellipse.

In some embodiments, the calculation module 204 performs the MCHT in logarithmic time. For example, the user interface 206 includes an option where the user can set one dimension while the other dimension works in O(log n) space. In addition, the user interface 206 includes an option to specify any part of the visual field to apply the MCHT, which can result in a more efficient process than traditional algorithms that randomly populate a Cartesian grid.

In some embodiments, the calculation module 204 receives data from the processing module 202 that originates at the VR headset 110 that includes imaging and VR capabilities, such as a modular system. The data may be received from a previous module of the VR headset 110 and the data can be used to even further inform MCHTs. For example, if a patient receives retinal imaging first on a modular headset, and a retinal deformity that would likely underlie a visual defect (such as a scotoma) is identified, then this data can be utilized in a future VR module application by prioritizing the presentation of stimulus points that coincide with the visual field of that deformed region. This demonstrates the benefits of a modular ophthalmic system, as one can make tests more efficient through utilization of extraocular (eye-tracking analysis of eyelid structure) and intraocular (retinal imaging analysis) data.

The calculation module 204 may determine a margin to reflex distance (MRD), which is the distance between the center of the pupil and the upper eyelid directly above the pupil. MRD is useful in corroborating visual field measurements and binning ptosis patients into severity grades as follows: mild (MRD=3-4 mm), moderate (MRD=2-3 mm), and severe (MRD=<2 mm).

In some embodiments, the calculation module 204 receives images of the eye from the processing module 202, which received the images from eye-tracking cameras. The calculation module 204 may approximate the degree of ptosis by estimating the pupil center and size and calculate the relative change in area compared to a normal, contralateral eye. The calculation module 204 may use an ellipse model to segment the pupil contour through binarization, thresholding methods, edge filtering, and intensity gradients, among other methods. The calculation module 204 can determine the bounds of the upper and lower eyelids using the visible pupil contour and the MRD can be subsequently estimated using the coordinates of the pupil center and approximation of the upper eyelid. The calculation module 204 may determine the degree of ptosis by comparing the MRD results to the contralateral eye to estimate vision loss due to ptosis.

In some embodiments, the calculation module 204 may alternatively perform eyelid detection directly without the secondary approximation (e.g., by performing MRD) by using pupil contour by leveraging intensity changes around eyelid edges. In some embodiments, the calculation module 204 maps the contours of the upper and lower eyelids using intensity gradients, for example, by identifying points that have a maximum respond to eyelid filters, fitting polynomials to eye corners to maximize an objective function dependent on intensity and area, and identifying points along a line that correspond to peaks on an intensity histogram. Any such approach can identify the coordinates of upper and lower eyelids, which can then be leveraged with respect to the contralateral eye to determine a percent change in vision.

Figure 5:
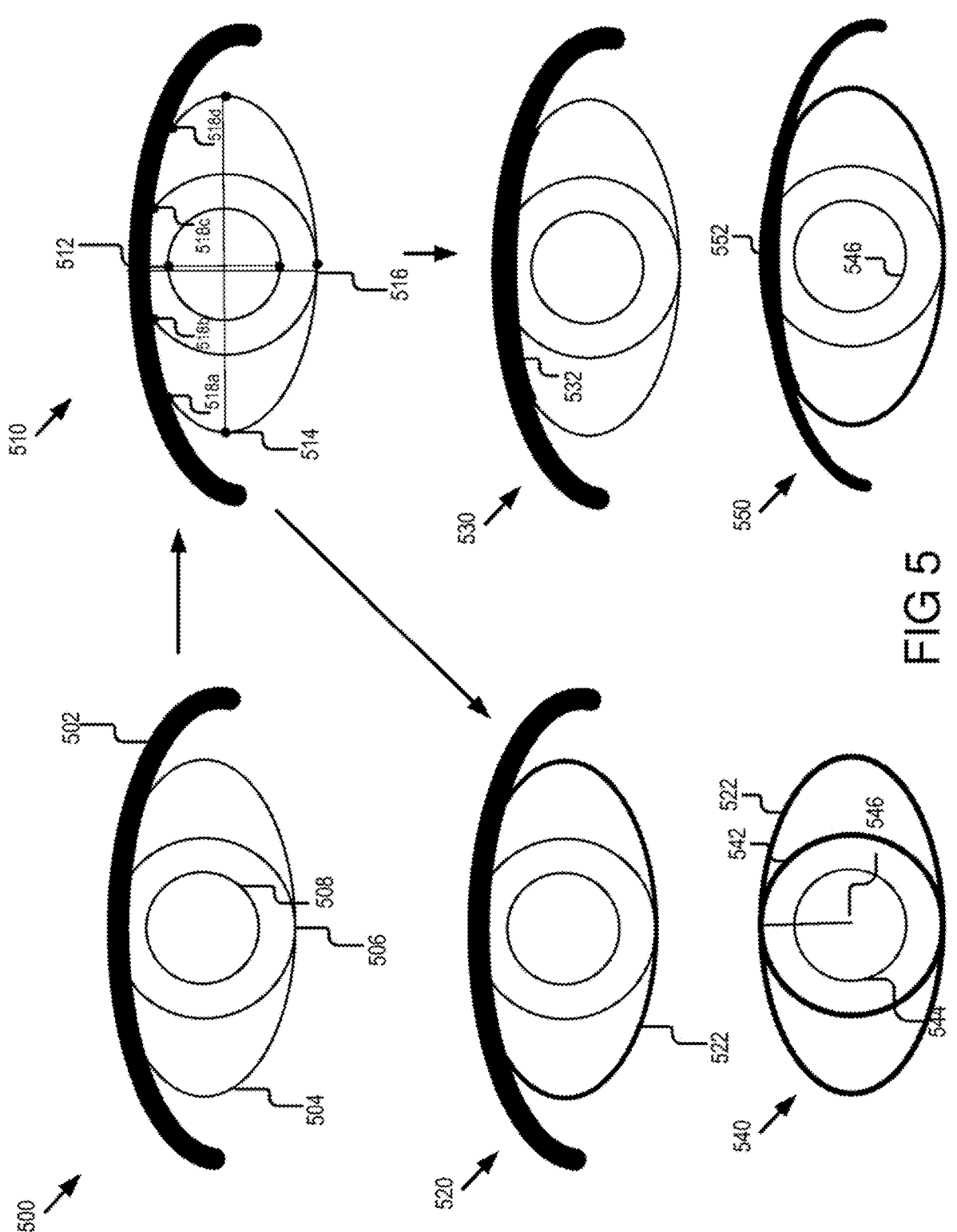
FIG. 5 illustrates a margin-to-reflex distance calculation from an external image of the eye, elliptical superposition with an eye-tracking camera, and MCHT optimization, according to some embodiments.

Turning to FIG. 5, a MRD calculation from an external image of the eye, elliptical superposition with an eye-tracking camera, and MCHT optimization is illustrated. Image 500 includes an exterior of the eye includes an upper eyelid 502 of the patient, a visible sclera 504 of the patient, an outer boundary 506 of the patient's iris, and an outer boundary 508 of the patient's pupil.

The calculation module 204 maps out anatomical landmarks for the eyelid meridian and predicts a pupil sphere and an iris sphere. Image 510 includes a diameter 512 of the patient's pupil as measured by eye-tracking cameras, a measurement 514 of an ellipse long axis diameter of a patient's sclera, a measurement 516 of an ellipse short axis diameter of a patient's sclera, and points 518a, 518b, 518c, 518d to form an arc of the patient's upper eyelid.

The calculation module 204 predicts an ellipse for the sclera based on short-axis and long-axis symmetry. Image 520 includes a predicted elliptical shape 522 of the sclera.

Image 530 illustrates an arc 532 that is mapped out by the calculation module 204. In some embodiments, the calculation module 204 is part of the VR headset 110 and the algorithm for calculating the arc 532 is reflection-based.

Image 540 illustrates the resulting calculations where a theoretical max MRD1 is 5 mm. The example image 540 shows the predicted elliptical shape 522 of the sclera, a calculated iris circumference 542, a pupil circumference 544, and a theoretical maximum MRD 546 for the patient, which is defined as the top boundary of the eyelid to the middle of the pupil (radius of the pupil).

Image 550 illustrates the approximate area 552 of the sclera that is covered by the eyelid and the theoretical maximum MRD 546 for the patient. The calculation module 206 determines the approximate area 552 of the sclera that is obscured by the upper eyelid by subtracting the areas of the ellipse with and without the arc of the upper eyelid 532. In some embodiments, the area of the ellipse is calculated as the following formula:

$$A = \pi ab \qquad \text{Formula 1}$$

Where a is a length of the long axis and b is a length of the short axis. In some embodiments, the calculation module 204 uses the MRD for MCHT optimization, as described in greater detail below.

In some embodiments, the MCHT and MRD calculations are used for assessing eye health. For example, the MCHT may be used in conjunction with a Humphrey Visual Field Analyzer (manufactured by Zeiss), which is a tool for measuring the human visual field. In another example, the MCHT may be used in conjunction with an Octopus (Manufactured by Heidelberg), which is used to measure and evaluate a patient's visual field. In yet another example, the MCHT/MRD calculations may be used for brain pathologies, such as stroke or multiple sclerosis; ocular conditions, such as glaucoma or age-related macular degeneration (AMD); or musculoskeletal conditions, such as ptosis. Many of the conditions that can cause ptosis are benign, such as age or a naturally larger eyelid, but there are some significant findings for ptosis that can be commonly missed, such as Homer's Syndrome (which can be from a stroke, tumor, or other neuro injury), myasthenia gravis, or diabetes. The application of the MCHT to allow providers across all fields to screen for these conditions when the degree of ptosis may not be obvious, will enable a faster and more comprehensive screening modality. In some embodiments, pairing the MCHT/MRD calculations with healthcare data analysis may be sued to identify which patients are at a higher risk of ptosis. For example, female diabetic patients may be identified through this method when conventional methods would result in a missed diagnosis opportunity.

In some embodiments, the calculation module 204 determines MRD by defining the center of the pupil as the center of the visual field and the center of the anterior portion of the eye relative to the orbit, serving as a predictive anchor point. The calculation module 204 approximates the perimeter of the eye by measuring the curvature of the visible sclera and using a Ramanujan calculation to artificially complete and approximate an ellipse and calculate the two-dimensional surface area using the following formula:

$$= \pi[3(a+b) - \sqrt{(3a+b)^*(a+3b)}] \qquad \text{Formula 2}$$

where a is a length of the long axis of the ellipse and b is a length of the short axis.

The calculation module 204 determines the bounds of the upper eyelid by infrared mapping and converting the lower lid to Cartesian coordinates and calculating the area by using the area underneath the curve (AUC) or the Trapezoidal rule. The calculation module 204 overlays the contralateral circle and eyelid on the diseased eye and selects the bounds of the ptotic eyelid. The calculation module 204 determines an MRD between the center of the pupil and both eyelid overlays to predict the percent visual field loss. This quantification method enables vision specialists to obtain measurements of the eyelid with respect to the pupil, inferior eyelid, and other anatomical markers in conjunction with eye tracking.

In some embodiments, the calculation module 204 increases the efficiency of the MCHT in real-time and improves the output accuracy of the MCHT. The calculation module 204 can use the Cartesian coordinates of the upper eyelid to bound the space of points relative to the curvilinear arc to increase precision of the meridian and reduce time for its localization. In some embodiments, the calculation module 204 calculates the upper or lower eyelid meridian by mapping out the superior/inferior most parts of the visual field.

The MCHT improves upon the precision of a standard visual field algorithm (such as the SITA/SITA-fast). Traditional visual field analysis techniques have fixed degrees of separation between stimuli (e.g., six-degree separation as seen in a 24-2) and are thus innately limited by that separation in screening and diagnostic power. The MCHT can screen through the entire visual field more rapidly than a traditional randomization algorithm and appropriately populate possible disease-state areas and depopulate physiologically normal areas of the visual field. For example, if a patient presents with a monocular scotoma located in their superior visual field at x=3, y=12 degrees with no other physiologic anomalies, a standard 24-2 screening would take around 5-10 minutes for that eye, resolving the scotoma at (3,12); however, no further information would be gathered without additional imaging and there exists no commercial screening algorithms for specified locations in the eye. Based on the clinical work that has been performed with the MCHT in VR headsets, the use of dynamic recursion can screen the superior field in 78 seconds as opposed to several minutes with existing technologies. Furthermore, if a physician wanted to explore the size of the affected area, further bounding of the algorithm around (3,12)+/–n degrees is possible to maximize the precision for each specific pathology. This algorithm can be employed in several technology modalities, including but not limited to existing perimeters, computational devices (such as laptops, smartphones, or tablets), VR/augmented reality (AR) headsets, and pre-commercial headset technologies, such as the modular headset described in PCT/US21/27544.

In some embodiments, the calculation module 204 can use the MCHT as an additive algorithm rather than a replacement for traditional visual screening algorithms if vision specialists wished to look at various areas of the visual field, corresponding to the retina. For example, after retinal detachment repair, the surgeon may wish to only test one part of the visual field with high precision rather than the entire visual field with low precision as currently offered commercially. The calculation module 204 could use the MCHT output along traditional retinal/fundus imaging to provide a combination of both anatomical and functional data for a patient's eye health.

In some embodiments, the calculation module 204 may further analyze the data using machine-learning algorithms for disease archetyping based on patient demographic information, ophthalmic information (e.g., visual fields and anatomical ocular data), and other patient health information. The calculation module 204 may further quantify and analyze this data to provide a holistic view of the patient's individual health and the patient's health relative to the population. In some embodiments, the calculation module 204 gathers physiological data in real time from other sources and provide real-time analysis for providers to improve their treatments for patients and patient populations.

The user interface module 206 generates a user interface. In some embodiments, the user interface module 206 includes a set of instructions executable by the processor 235 to generate the user interface. In some embodiments, the user interface module 206 is stored in the memory 237 of the computing device 200 and can be accessible and executable by the processor 235.

In some embodiments, the user interface module 206 generates options for a user to configure parameters for implementing the MCHT. The user interface module 206 may include options for defining boundaries of a vertical axis, a horizontal axis, or a planar axis. For example, the user may select to define the boundaries based on results from the MRD analysis. The user interface module 206 may include options for defining a degree offset of each of the columns relative to tested points to enable full or partial visual field analysis. For example, the degree offset may be one degree. The user interface module 206 may include options for defining x-axis and y-axis bounds and the MCHT can grid search within the spatial parameters. For example, the x-axis may be the length of the ellipse long axis diameter of patient sclera as determined by the MRD analysis. In another example, the bounds could be 24 degrees, 30 degrees, etc. The user interface module 206 may include options for defining a type of displayed coordinate system where the coordinate system may include Cartesian, polar, spherical, or orthogonal curvilinear coordinates.

Example Flowcharts

Figure 6:
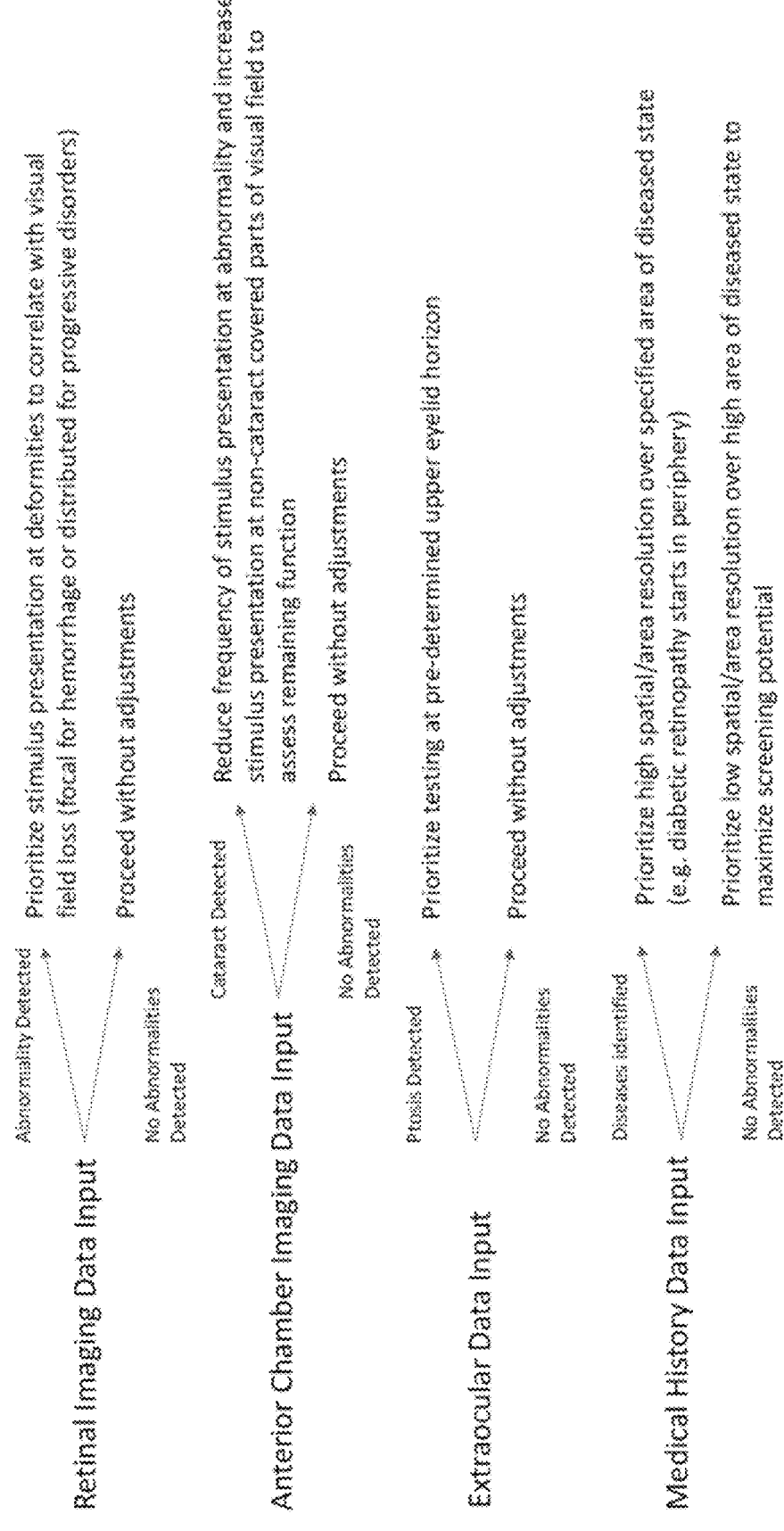
FIG. 6 illustrates an MCHT optimization flowchart, according to some embodiments.

FIG. 6 illustrates an MCHT optimization flowchart 600 that includes types of output data based on different types of input data. In a first example, for retinal imaging data input, if an abnormality is detected, the vision application 103 prioritizes stimulus presentation at deformities to correlate with visual field loss (focal for hemorrhage or distributed for progressive disorders). If no abnormality is detection, the vision application 103 proceeds without adjustments.

In a second example, for anterior chamber imaging data input, if a cataract is detected, the vision application 103 reduces frequency of stimulus presentation at abnormality and increases stimulus presentation at non-cataract covered parts of the visual field to assess remaining function. If no abnormalities are detected, the vision application 103 proceeds without adjustments.

In a third example, for extraocular data input, if ptosis is detected, the vision application 103 prioritizes testing at a pre-determined upper eyelid horizon. If no abnormalities are detected, the vision application 103 proceeds without adjustments.

In a fourth example, for medical history data input, if diseases are identified, the vision application 103 prioritizes high spatial/area resolution over a specified area of diseased state (e.g., diabetic retinopathy starts in the periphery). If no abnormalities are detected, the vision application 103 prioritizes low spatial/area resolution over a high area of diseased state to maximize screening potential.

Figure 7B:
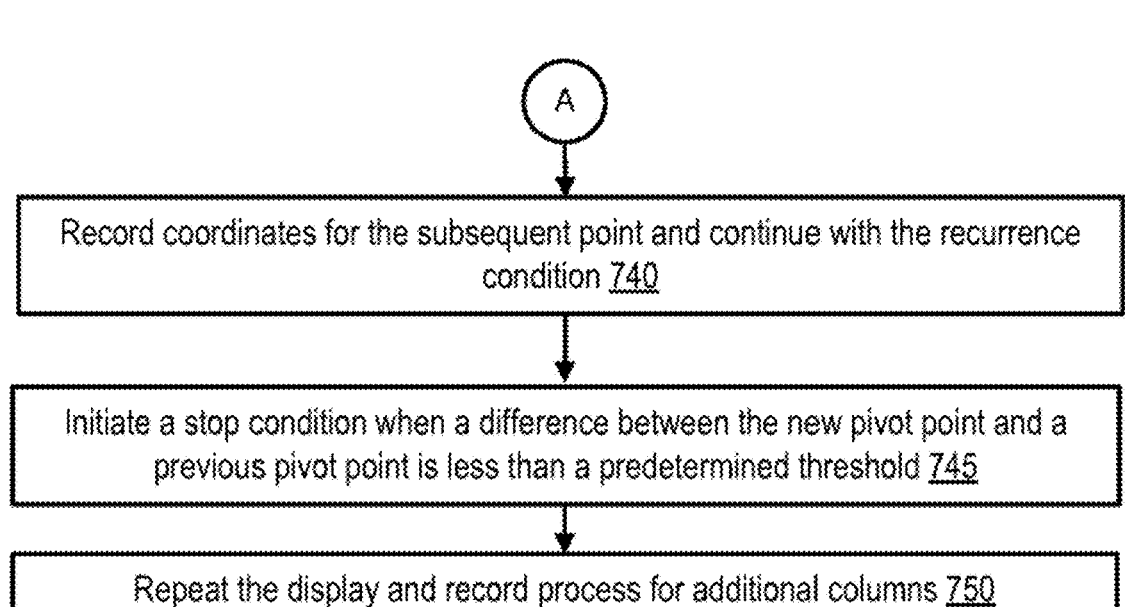

FIGS. 7A-B illustrates an example flowchart 700 for calculating MCHT, according to some embodiments. The method illustrated in flowchart 700 may be performed by the computing device 200 in FIG. 2. In some embodiments, the computing device 200 is the VR headset 110 in FIG. 1. In some embodiments, the computing device 200 is the vision server 101 in FIG. 1. In some embodiments, the computing device 200 is the user device 115 in FIG. 1. In some embodiments, the steps of flowchart 700 are performed by one or more of the VR headset 110, the vision server 101, and the user device 115.

The method 700 may begin at block 705. At block 705, a superior visual field is defined as rows and columns in a coordinate system. Block 705 may be followed by block 710.

At block 710, a display and record process is performed for a first column of the columns. Block 710 may be followed by block 715. At block 715, a base condition is initiated that includes displaying, to a patient, a start point in a first column of the columns, where an upper bound of the first column is a highest row in the first column, a lower bound is a lowest row in the first column, and an initial pivot point is between the upper bound and the lower bound. Block 715 may be followed by block 720. At block 720 it is determined whether the patient can see the start point.

If the patient cannot see the start point, block 720 may be followed by block 725 where a recurrence condition is initiated that includes defining a new pivot point as the upper bound and displaying to the patient a second point in the first column between the lower bound and the new pivot point. For example, the new pivot point is displayed half-way between the lower bound and the new pivot point.

If the patient can see the start point, block 720 may be followed by block 730 where the recurrence condition is initiated that includes defining the new pivot point as the lower bound, recording coordinates for the start point, and displaying to the patient a subsequent point in the first column between the upper bound and the new pivot point. For example, the subsequent point may be displayed half-way between the upper bound and the new pivot point. Block 730 may be followed by block 735.

At block 735, it is determined whether the patient can see the subsequent point. If the patient cannot see the subsequent point, block 735 may be followed by block 730. If the patient can see the subsequent point, block 735 may be followed by block 740. At block 740, coordinates are recorded for the subsequent point and the method 700 continues with the recurrence condition. Block 740 may be followed by block 745.

At block 745, a stop condition is initiated when a difference between the new pivot point and a previous pivot point is less than a predetermined threshold. Block 745 may be followed by block 750.

At block 750, the display and record process is repeated for additional columns. For example, the display and record process is repeated for each column of the columns.

Figure 8:
FIG. 8 illustrates another telemedicine flowchart for ptosis patients, according to some embodiments.
Figure 8:
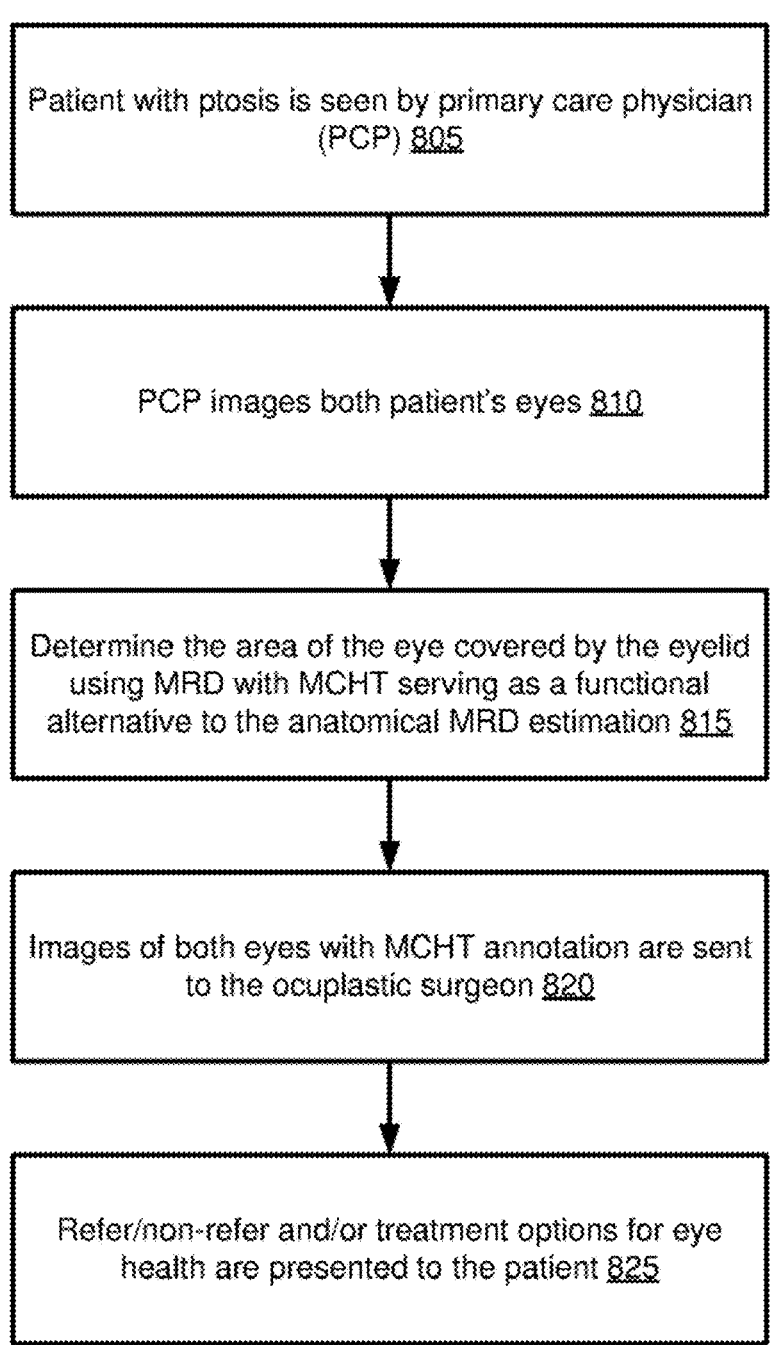

FIG. 8 illustrates a telemedicine flowchart 800 for ptosis patients, according to some embodiments. Method 800 may begin at block 805. At block 805, a patient with ptosis is seen by a primary care physician (PCP). At block 810, the PCP images both patient's eyes. The PCP may use a VR headset, such as a modular VR headset with eye-tracking cameras to image the patient's eyes. Eye-tracking cameras can be used to accelerate VR tests by predetermining ocular abnormalities such as eyelid droop and reducing the need to provide stimuli to areas that are known to be healthy or diseased, depending on the goal of teach test.

At block 815, the area of the eye covered by the eyelid is determined using MRD with MCHT serving as a functional alternative to the anatomical MRD estimation. By measuring the fixation/fixation loss of a patient during the imaging, the provider is able to provide more accurate analyses of the examiner as valid/invalid.

At block 820, images of both eyes with MCHT annotation are sent to an oculoplastic surgeon. For example, the MCHT annotation may include an indication of a percentage of visual field loss in the affected eye. In some embodiments, the MCHT is administered to compare the functional visual data against the anatomical data and overlap between the two to provide the oculoplastic surgeon with multidimensional data for the ptosis patient.

At block 825, refer/non-refer and/or treatment options for eye health are presented to the patient and/or the PCP. For example, eye surgery may be recommended to correct for ptosis.

FIG. 9 illustrates another telemedicine model for ptosis patients, according to some embodiments. In some embodiments, tests including visual fields (e.g, MCHT), MRD calculation, retinal imaging, and anterior chamber imaging (in conjunction or individually) are performed remotely by non-specialized healthcare practitioners (e.g., nurses, technicians, physicians assistants, or physicians). Test results may be sent to specialists, such as ophthalmologists and oculoplastic surgeons for consultation and treatment decisions. The techniques described above advantageously reduce time-to-decision and time-to-treatment by employing these techniques remotely. Method 900 may begin at block 905.

At block 905, eye images are received remotely using VR, AR, or from another digital device. At block 910, MCHT and MRD calculations are performed in real time and delivered to a remote oculoplastic surgeon. Traditionally, oculoplastic surgeons take their own MRD measurements, which are associated with a lot of variability depending on the provider, the position of the patient, and other stochastic factors. As a result of this technology, the oculoplastic surgeons no longer need to take their own measurements. As a result of having a streamlined process for calculating the MRD, the subjectivity of these measurements is reduced. In FIG. 9, the bracket in the eye to the right of block 910 represents the MRD1 measurement of 1 mm, which is a severe classification.

At block 915, a direct care recommendation and referral is provided for corrective surgery since the four criteria for ptosis corrective surgery can be measured using the MCHT and MRD calculations.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the embodiments can be described above primarily with reference to user interfaces and particular hardware. However, the embodiments can apply to any type of computing device that can receive data and commands, and any peripheral devices providing services.

Reference in the specification to "some embodiments" or "some instances" means that a particular feature, structure, or characteristic described in connection with the embodiments or instances can be included in at least one implementation of the description. The appearances of the phrase "in some embodiments" in various places in the specification are not necessarily all referring to the same embodiments.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic data capable of being stored, transferred, combined, compared, and otherwise manipulated. It has proven convenient at times, principally for reasons of common usage, to refer to these data as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The embodiments of the specification can also relate to a processor for performing one or more steps of the methods described above. The processor may be a special-purpose processor selectively activated or reconfigured by a computer program stored in the computer. Such a computer program may be stored in a non-transitory computer-readable storage medium, including, but not limited to, any type of disk including optical disks, ROMs, CD-ROMs, magnetic disks, RAMs, EPROMs, EEPROMs, magnetic or optical cards, flash memories including USB keys with non-volatile memory, or any type of media suitable for storing electronic instructions, each coupled to a computer system bus.

The specification can take the form of some entirely hardware embodiments, some entirely software embodiments or some embodiments containing both hardware and software elements. In some embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

What is claimed is:

1. A computer-implemented method to predict visual field loss, the method comprising:

defining a superior visual field as rows and columns in a coordinate system;

performing a display and record process for a first column of the columns by:

initiating a base condition that includes displaying, to a patient, with a virtual reality (VR) headset a start point in the first column of the columns, wherein an upper bound of the first column is a highest row in the first column, a lower bound is a lowest row in the first column, and an initial pivot point is between the upper bound and the lower bound;

receiving input indicative of whether the start point is visible to the patient, wherein the VR headset includes a trigger pull that is configured to be activated by the patient or an audio interface that is configured to record audio from the patient to provide the input indicative of whether the start point is visible to the patient;

initiating a recurrence condition where responsive to a determination that the patient can see the start point, defining a new pivot point as the lower bound, recording coordinates for the start point, and displaying to the patient a subsequent point in the first column between the upper bound and the new pivot point;

receiving input indicative of whether the subsequent point is visible to the patient;

responsive to the patient seeing the subsequent point, recording coordinates for the subsequent point and continuing with the recurrence condition; and initiating a stop condition when a difference between the new pivot point and a previous pivot point is less than a predetermined threshold;

repeating the display and record process for additional columns of the columns;

defining an eyelid meridian based on recorded coordinates for a set of points that are visible to the patient;

calculating an area of the superior visual field based on the eyelid meridian; and determining the visual field loss based the area of the superior visual field.

2. The method of claim 1, further comprising:

responsive to the patient not seeing the start point, defining the new pivot point as the upper bound and displaying to the patient a second point in the first column between the lower bound and the new pivot point; and responsive to the patient seeing the second point, recording coordinates for the second point and continuing with the recurrence condition.

3. The method of claim 1, the method further comprising after the stop condition is initiated, displaying an additional point above coordinates for the stop condition and an additional point below coordinates for the stop condition to confirm the stop condition.

4. The method of claim 3, the method further comprising responsive to the patient not seeing one or more of the additional point above the coordinates for the stop condition and the additional point below the coordinates for the stop condition, returning to the recurrence condition until the stop condition is reached again.

5. The method of claim 1, wherein the display and record process for the additional columns of the columns is performed to determine a first superior visual field with no ptosis when an eyelid is taped and a second superior visual field with ptosis when the eyelid is not taped.

6. The method of claim 1, further comprising:

receiving eye images remotely, wherein the display and record process is performed based on the eye images; and transmitting the recorded coordinates and the visual field loss to a remote oculoplastic surgeon.

7. The method of claim 1, wherein the coordinates for the set of points are automatically recorded by eye-tracking cameras.

8. The method of claim 7, wherein the eye-tracking cameras include infrared (IR) cameras or near infrared (NIR) cameras.

9. The method of claim 1, further comprising prior to defining the superior visual field:

determining a margin to reflex distance (MRD) and Cartesian coordinates for an upper eyelid relative to a curvilinear arc of the upper eyelid; and selecting a set of candidate points to be shown to the patient based on the MRD.

10. The method of claim 1, further comprising generating a user interface that includes options to define one or more of: boundaries of a vertical axis, a horizontal axis, or a planar axis; a degree offset of each of the columns relative to tested points; x-axis and y-axis bounds; and the coordinate system as Cartesian, polar, spherical, or orthogonal curvilinear coordinates.

11. The method of claim 1, wherein the visual field loss is used to assess eye health for one or more of a brain pathology, an ocular condition, or a musculoskeletal condition and wherein the recorded coordinates are combined with healthcare data analysis to identify when the patient is at higher risk of ptosis.

12. The method of claim 1, wherein determining the visual field loss is based on a Ramanujan calculation to approximate a predicted field of an eyeball.

13. A system to predict visual field loss comprising:
a processor; and
a memory coupled to the processor, with instructions
stored thereon that, when executed by the processor,
cause the processor to perform operations comprising:
defining a superior visual field as rows and columns in
a coordinate system;
performing a display and record process for a first
column of the columns by:
initiating a base condition that includes displaying,
to a patient, with a virtual reality (VR) headset a
start point in the first column of the columns,
wherein an upper bound of the first column is a
highest row in the first column, a lower bound is
a lowest row in the first column, and an initial
pivot point is between the upper bound and the
lower bound;
receiving input indicative of whether the start point
is visible to the patient, wherein the VR headset
includes a trigger pull that is configured to be
activated by the patient or an audio interface that
is configured to record audio from the patient to
provide the input indicative of whether the start
point is visible to the patient;
initiating a recurrence condition where responsive to
a determination that the patient can see the start
point, defining a new pivot point as the lower
bound, recording coordinates for the start point,
and displaying to the patient a subsequent point in
the first column between the upper bound and the
new pivot point;
receiving input indicative of whether the subsequent
point is visible to the patient;
responsive to the patient seeing the subsequent point,
recording coordinates for the subsequent point and
continuing with the recurrence condition; and
initiating a stop condition when a difference between
the new pivot point and a previous pivot point is
less than a predetermined threshold;
repeating the display and record process for additional
columns of the columns;
defining an eyelid meridian based on recorded coordi-
nates for a set of points that are visible to the patient;
calculating an area of the superior visual field based on
the eyelid meridian; and
determining the visual field loss based the area of the
superior visual field.
14. The system of claim 13, further comprising a display
and one or more eye-tracking cameras, wherein the system
is a virtual reality headset or an augmented reality headset.
15. The system of claim 13, wherein the operations further
comprise:
responsive to the patient not seeing the start point, defin-
ing the new pivot point as the upper bound and dis-
playing to the patient a second point in the first column
between the lower bound and the new pivot point; and
responsive to the patient seeing the second point, record-
ing coordinates for the second point and continuing
with the recurrence condition.
16. The system of claim 13, wherein the operations further
comprise after the stop condition is initiated, displaying an
additional point above coordinates for the stop condition and
an additional point below coordinates for the stop condition
to confirm the stop condition.
17. A non-transitory computer-readable medium with
instructions stored thereon to predict visual field loss that, when executed by one or more computers, cause the one or
more computers to perform operations, the operations com-
prising:
defining a superior visual field as rows and columns in a
coordinate system;
performing a display and record process for a first column
of the columns by:
initiating a base condition that includes displaying, to a
patient, with a virtual reality (VR) headset a start
point in the first column of the columns, wherein an
upper bound of the first column is a highest row in
the first column, a lower bound is a lowest row in the
first column, and an initial pivot point is between the
upper bound and the lower bound;
receiving input indicative of whether the start point is
visible to the patient, wherein the VR headset
includes a trigger pull that is configured to be acti-
vated by the patient or an audio interface that is
configured to record audio from the patient to pro-
vide the input indicative of whether the start point is
visible to the patient;
initiating a recurrence condition where responsive to a
determination that the patient can see the start point,
defining a new pivot point as the lower bound,
recording coordinates for the start point, and display-
ing to the patient a subsequent point in the first
column between the upper bound and the new pivot
point;
receiving input indicative of whether the subsequent
point is visible to the patient;
responsive to the patient seeing the subsequent point,
recording coordinates for the subsequent point and
continuing with the recurrence condition; and
initiating a stop condition when a difference between
the new pivot point and a previous pivot point is less
than a predetermined threshold;
repeating the display and record process for additional
columns of the columns;
defining an eyelid meridian based on recorded coordinates
for a set of points that are visible to the patient;
calculating an area of the superior visual field based on the
eyelid meridian; and
determining the visual field loss based the area of the
superior visual field.
18. The computer-readable medium of claim 17, wherein
the operations further comprise:
responsive to the patient not seeing the start point, defin-
ing the new pivot point as the upper bound and dis-
playing to the patient a second point in the first column
between the lower bound and the new pivot point; and
responsive to the patient seeing the second point, record-
ing coordinates for the second point and continuing
with the recurrence condition.
19. The computer-readable medium of claim 17, wherein
the operations further comprise after the stop condition is
initiated, displaying an additional point above coordinates
for the stop condition and an additional point below coor-
dinates for the stop condition to confirm the stop condition.
20. The computer-readable medium of claim 19, wherein
the operations further comprise responsive to the patient not
seeing one or more of the additional point above the coor-
dinates for the stop condition and the additional point below
the coordinates for the stop condition, returning to the
recurrence condition until the stop condition is reached
again.

* * * * *